US00PP21229P2

(12) United States Plant Patent
Lemon

(10) Patent No.: US PP21,229 P2
(45) Date of Patent: Aug. 24, 2010

(54) *GERANIUM* PLANT NAMED 'OGLGER11154'

(50) Latin Name: *Pelargonium×hortorum*
Varietal Denomination: Oglger11154

(75) Inventor: David Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 39 days.

(21) Appl. No.: 12/316,454

(22) Filed: Dec. 12, 2008

(51) Int. Cl.
*A01H 5/00* (2006.01)

(52) U.S. Cl. ..... Plt./330

(58) Field of Classification Search ..... Plt./330
See application file for complete search history.

*Primary Examiner*—Wendy C. Haas
(74) *Attorney, Agent, or Firm*—C.A. Whealy

(57) ABSTRACT

A new and distinct cultivar of Zonal *Geranium* plant named 'Oglger11154', characterized by its upright, outwardly spreading and mounded plant habit; freely branching habit; freely and early flowering habit; bright scarlet red-colored flowers; and good garden performance.

1 Drawing Sheet

Botanical designation: *Pelargonium×hortorum*.
Cultivar denomination: 'OGLGER11154'.

BACKGROUND OF THE INVENTION

The present invention relates to a new and distinct cultivar of Zonal *Geranium* plant, botanically known as *Pelargonium×hortorum*,and hereinafter referred to by the name 'Oglger11154'.

The new Zonal *Geranium* plant is a product of a planned breeding program conducted by the Inventor in Lompoc, Calif. The objective of the breeding program is to create new compact Zonal *Geranium* cultivars with zoned dark green-colored foliage and attractive flower coloration.

The new Zonal *Geranium* originated from a cross-pollination made by the Inventor in June, 2000 in Lompoc, Calif. of *Pelargonium×hortorum* 'Patriot Red', disclosed in U.S. Plant Pat. No. 13,516, as the female, or seed, parent with a proprietary selection of *Pelargonium×hortorum* identified as code number 8217, not patented, as the male, or pollen, parent. The new Zonal *Geranium* was discovered and selected by the Inventor as a single flowering plant from within the progeny of the stated cross-pollination in a controlled greenhouse environment in Lompoc, Calif. in March, 2001.

Asexual reproduction of the new Zonal *Geranium* plant by vegetative terminal cuttings in a controlled greenhouse environment in Connellsville, Pa. since January, 2002, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglger11154'. These characteristics in combination distinguish 'Oglger11154' as a new and distinct cultivar of Zonal *Geranium*:

1. Upright, outwardly spreading and mounded plant habit.
2. Freely branching habit.
3. Freely and early flowering habit.
4. Bright scarlet red-colored flowers.
5. Good garden performance.

Plants of the new Zonal *Geranium* differ from plants of the female parent, 'Patriot Red', in the following characteristics:

1. Plants of the new Zonal *Geranium* are more freely flowering than plants of 'Patriot Red'.
2. Plants of the new Zonal *Geranium* have longer peduncles than plants of 'Patriot Red'.

Plants of the new Zonal *Geranium* differ primarily from plants of the male parent selection primarily in flower color as plants of the male parent selection have cherry red-colored flowers.

Plants of the new Zonal *Geranium* can be compared to plants of *Pelargonium×hortorum* 'Fisfire', disclosed in U.S. Plant Pat. No. 12,489. In side-by-side comparisons conducted in Connellsville, Pa., plants of the new Zonal *Geranium* differed from plants of 'Fisfire' primarily in flower color as plants of 'Fisfire' had lighter scarlet-colored flowers. In addition, plants of the new Zonal *Geranium* flowered earlier than plants of 'Fisfire'.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*.

The photograph comprises a side perspective view of a typical flowering plant of 'Oglger11154' grown in a container.

DETAILED BOTANICAL DESCRIPTION

The aforementioned photograph and following observations, measurements and values describe plants grown in Connellsville, Pa. in a glass-covered greenhouse during the summer and under conditions which closely approximate Zonal *Geranium* commercial production. During the production of the plants, day temperatures ranged from 21° C. to 32° C., night temperatures ranged from 17° C. to 21° C. and light levels ranged from 2,500 to 3,000 foot-candles. Plants had been growing for nine weeks when the photograph and the description were taken. In the detailed description, color references are made to The Royal Horticultural Society Colour Chart, 2001 Edition, except where general terms of ordinary dictionary significance are used.

Botanical classification: *Pelargonium×hortorum* 'Oglger11154'.

Parentage:

*Female, or seed, parent.*—*Pelargonium×hortorum* 'Patriot Red', disclosed in U.S. Plant Pat. No. 13,516.

*Male or pollen parent.*—Proprietary selection of *Pelargonium×hortorum* identified as code number 8217, not patented.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Fine, fibrous; white in color.

*Rooting habit.*—Freely branching.

Plant description:

*General appearance.*—Upright and outwardly spreading plant habit; uniformly mounded; densely foliated.

*Growth and branching habit.*—Moderately vigorous growth habit. Freely branching habit.

*Plant height, to top of foliar plane.*—About 21.7 cm to 26.2 cm.

*Plant height, to top of umbels.*—About 27.6 cm to 29.8 cm.

*Plant width.*—About 32.5 cm.

*Main stems.*—Length: About 2.4 cm to 3.6 cm. Diameter: About 7 mm to 9 mm. Internode length: About 1.4 cm to 3.2 cm. Texture: Smooth, glabrous. Strength: Strong. Color: Close to 144A.

*Primary lateral branches.*—Length: About 9.5 cm to 19.8 cm. Diameter: About 3 mm to 5 mm. Internode length: About 2.1 cm to 3.9 cm. Texture: Slightly pubescent. Strength: Strong. Color: Close to 144A.

Foliage description:

*Arrangement.*—Alternate, simple.

*Length.*—About 2.3 cm to 8.4 cm.

*Width.*—About 3.2 cm to 7.2 cm.

*Shape.*—Reniform.

*Apex.*—Rounded.

*Base.*—Cordate.

*Margin.*—Pedately-lobed; crenate.

*Venation pattern.*—Palmate.

*Texture, upper and lower surfaces.*—Slightly pubescent; leathery.

*Color.*—Developing foliage, upper surface: Close to 143A. Developing foliage, lower surface: Close to 146C. Fully expanded foliage, upper and lower surfaces: Close to 147B; venation, close to 147B. Zonation pattern: Distinct. Diameter: About 3 cm. Color: Close to 200D.

*Petiole.*—Length: About 2 cm to 2.2 cm. Diameter: About 1 mm to 1.5 mm. Texture, upper and lower surfaces: Smooth, glabrous. Color, upper and lower surfaces: Close to 146C.

Flower description:

*Flower arrangement.*—Rotate flowers arranged in rounded hemispherical umbels arising from apical leaf axils. Umbels displayed above the foliage on strong peduncles. Flowers face upright to outward; flowers slightly cupped becoming flatter with development. Flowers not persistent. Flowers not fragrant.

*Quantity of flowers.*—Freely flowering habit; about five to eight flowers per umbel and about one to eight umbels per lateral branch.

*Flowering season.*—In Connellsville, Pa., flowering is continuous during the spring and summer.

*Flower longevity.*—Individual flowers last about 10 to 14 days on the plant.

*Umbel height.*—About 2.9 cm to 3.5 cm.

*Umbel diameter.*—About 6.7 cm to 8.5 cm.

*Flower diameter.*—About 2.3 cm to 4.6 cm.

*Flower depth* (*height*).—About 9 mm to 14 mm.

*Flower buds.*—Length: About 2.6 cm to 3.4 cm. Diameter: About 4 mm to 8 mm. Shape: Elliptical.

*Petals.*—Quantity per flower: About ten to twelve. Length: About 2.6 cm to 2.8 cm. Width: About 1.3 cm to 1.5 cm. Shape: Roughly spatulate. Apex: Rounded. Base: Attenuate. Margin: Entire. Texture, upper and lower surfaces: Smooth, glabrous. Color: When opening and fully opened, upper surface: Close to N30A. When opening and fully opened, lower surface: Close to 42C.

*Petaloids.*—Quantity per flower: None to about two. Length: About 6 mm to 9 mm. Width: About 3 mm to 6 mm. Shape: Elongated, slender. Apex: Rounded. Base: Attenuate. Margin: Entire. Texture, upper and lower surfaces: Smooth, glabrous. Color: When opening and fully opened, upper surface: Close to N30A. When opening and fully opened, lower surface: Close to 42C.

*Sepals.*—Quantity per flower: Five, arranged in a single whorl. Length: About 2 cm. Width: About 5 mm. Shape: Lanceolate. Apex: Acute. Base: Attenuate. Margin: Entire. Color, upper and lower surfaces: Close to 144A.

*Peduncle* (*umbel stem*).—Length: About 11.6 cm to 15.1 cm. Diameter: About 2 mm to 3.5 mm. Strength: Strong. Texture: Pubescent. Color: Close to 146C.

*Pedicel* (*individual flower stem*).—Length: About 1.8 cm to 2.1 cm. Diameter: About 1 mm to 2 mm. Strength: Moderately strong. Texture: Pubescent. Color: Close to 144A.

*Reproductive organs.*—Androecium: Stamen quantity per flower: About six to eight. Filament length: About 5 mm to 9 mm. Filament color: Close to N155B. Anther length: About 1.5 mm to 2 mm. Anther shape: Oval. Anther color: Close to 156D. Pollen amount: Moderate to abundant. Pollen color: Close to 171B. Gynoecium: Pistil quantity per flower: One. Pistil length: About 9 mm Stigma shape: Split into six parts. Stigma size: About 2.5 mm. Stigma color: Close to 169C. Style length: About 2.5 mm. Style color: Close to 157A. Ovary color: Slightly darker than 157A.

*Seed.*—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate wind, and temperatures ranging from about 1° C. to about 35° C. and have demonstrated good garden performance.

It is claimed:

1. A new and distinct Zonal *Geranium* plant named 'Oglger11154' as illustrated and described.

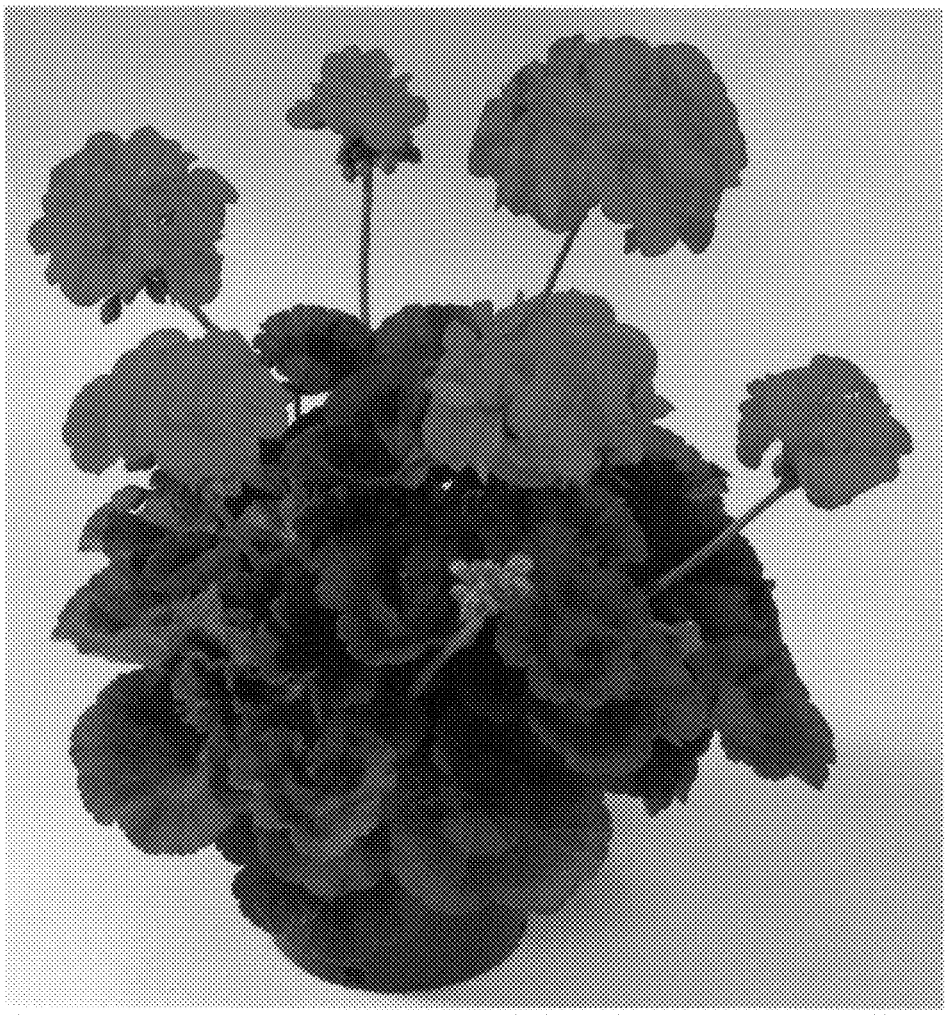

* * * * *